US012658283B2

(12) United States Patent
Severs et al.

(10) Patent No.: US 12,658,283 B2
(45) Date of Patent: Jun. 16, 2026

(54) PLATFORM FOR END-TO-END BIOPROCESS OUTPUT DATA ANALYSIS

(71) Applicant: Benchling, Inc., San Francisco, CA (US)

(72) Inventors: Chris Severs, San Francisco, CA (US); Nick Floeck, Marlton, NJ (US); Helen Liu-Mayo, Palo Alto, CA (US); Nari Kang, San Francisco, CA (US); Stephen Worlow, San Francisco, CA (US)

(73) Assignee: Benchling, Inc., San Francisco, CA (US)

( * ) Notice: Subject to any disclaimer, the term of this patent is extended or adjusted under 35 U.S.C. 154(b) by 0 days.

(21) Appl. No.: 18/972,730

(22) Filed: Dec. 6, 2024

(65) Prior Publication Data

US 2026/0162775 A1     Jun. 11, 2026

(51) Int. Cl.
*G16B 50/30* (2019.01)
*G16B 40/20* (2019.01)
*G16B 45/00* (2019.01)

(52) U.S. Cl.
CPC ............. *G16B 50/30* (2019.02); *G16B 40/20* (2019.02); *G16B 45/00* (2019.02)

(58) Field of Classification Search
None
See application file for complete search history.

(56) References Cited

U.S. PATENT DOCUMENTS 6,041,263  A     3/2000  Boston et al.
7,392,107  B2    6/2008  Popp
(Continued)

FOREIGN PATENT DOCUMENTS

CN     113721567  A     11/2021
EP        3122892          2/2017
(Continued)

OTHER PUBLICATIONS

Riley, Erin M., Holly Z. Hattaway, and P. Arthur Felse. "Implementation and use of cloud-based electronic lab notebook in a bioprocess engineering teaching laboratory." Journal of Biological Engineering 11 (2017): 1-9. (Year: 2017).*
Rubacha, Michael, Anil K. Rattan, and Stephen C. Hosselet. "A review of electronic laboratory notebooks available in the market today." JALA: Journal of the Association for Laboratory Automation 16.1 (2011): 90-98. (Year: 2011).*
(Continued)

*Primary Examiner* — Karlheinz R. Skowronek
*Assistant Examiner* — Mary C Leverett
(74) *Attorney, Agent, or Firm* — Fish & Richardson P.C.

(57) ABSTRACT

Methods, systems, and apparatus, including computer programs encoded on a computer storage medium, for automatic or semi-automatic end-to-end data analysis of bioprocess output data. In particular, using a bioinformatics platform subsystem in conjunction with a laboratory computer subsystem and an electronic laboratory notebook subsystem for automatic analysis of bioprocess output data within a unified platform system. The platform system receives user input that includes a request to perform an automatic analysis process and ultimately updates an electronic laboratory notebook entry that includes output data generated by the analysis. Because the platform system is capable of in real-time automatic handling of a plurality of datasets types from a plurality of bioprocesses, the system can simplify and accelerate bioprocess output data analysis and can be used in feedback-driven optimization of bioprocess procedures.

17 Claims, 7 Drawing Sheets

(56) References Cited

U.S. PATENT DOCUMENTS

| | | | |
|---|---|---|---|
| 8,738,190 | B2 | 5/2014 | Pai et al. |
| 9,226,875 | B2 | 1/2016 | Foshee et al. |
| 10,088,837 | B1 | 10/2018 | Strain et al. |
| 10,656,628 | B2 | 5/2020 | Feiten et al. |
| 10,671,035 | B2 | 6/2020 | Feiten et al. |
| 11,079,896 | B2 | 8/2021 | Sciola et al. |
| 11,086,302 | B2 | 8/2021 | Marruchella et al. |
| 11,200,031 | B2 | 12/2021 | Holbrook et al. |
| 11,340,876 | B2 | 5/2022 | Kim et al. |
| 2002/0052862 | A1 | 5/2002 | Scott et al. |
| 2007/0050070 | A1 | 3/2007 | Strain et al. |
| 2008/0097623 | A1 | 4/2008 | Weatherhead et al. |
| 2009/0299511 | A1 | 12/2009 | Chan et al. |
| 2013/0144591 | A1 | 6/2013 | Khan |
| 2020/0348662 | A1 | 11/2020 | Cella et al. |
| 2021/0406461 | A1* | 12/2021 | Kwon ..................... G06N 5/01 |
| 2023/0050810 | A1* | 2/2023 | Miller .............. G05B 19/41865 |
| 2023/0168662 | A1 | 6/2023 | Stacey et al. |
| 2024/0385600 | A1 | 11/2024 | Pieri et al. |

FOREIGN PATENT DOCUMENTS

| | | | |
|---|---|---|---|
| WO | WO 2006040134 A1 | 4/2006 | |
| WO | WO 2015148530 A1 | 10/2015 | |
| WO | WO-2022216970 A1 * | 10/2022 | ........... G06F 16/168 |
| WO | WO-2024249903 A1 * | 12/2024 | ......... G01N 35/0092 |

OTHER PUBLICATIONS

U.S. Appl. No. 18/807,846, Kimball, filed Aug. 16, 2024.

Atlassian.com [online], "All great projects start with Jira," available on or before Aug. 18, 2024, via Internet Archive: Wayback Machine URL <https://web.archive.org/web/20240818005116/https://www.atlassian.com/software/jira>, retrieved on Aug. 22, 2024, URL<https://www.atlassian.com/software/jira>, 11 pages.

Camunda.com [online], "What is BPMN? Business Process Model and Notation," available on or before Apr. 7, 2023, via Internet Archive: Wayback Machine URL <https://web.archive.org/web/20230407162138/https://camunda.com/bpmn/>, retrieved on Aug. 22, 2024, URL<https://camunda.com/bpmn/s>, 12 pages.

Google.com [online], "Build your best ideas together, in Google Docs," available on or before Jan. 13, 2022, via Internet Archive: Wayback Machine URL <https://web.archive.org/web/20220113040742/https://www.google.com/docs/about/>, retrieved on Aug. 22, 2024, URL<https://www.google.com/docs/about/>, 11 pages.

Piccione et al., "Systematizing scientific laboratory work by a workflow and template for electronic laboratory notebooks," Education for Chemical Engineers, Apr. 2020, 31:42-53.

Servicenow.com [online], "Put AI to Work With ServiceNow," available on or before Jul. 1, 2024, via Internet Archive: Wayback Machine URL <https://web.archive.org/web/20240701042617/https://www.servicenow.com/>, retrieved on Aug. 22, 2024, URL<https://www.servicenow.com/>, 7 pages.

Skylandanalytics.net [online], "Introducing Skyland PIMS®," available on or before Aug. 22, 2024, via Internet Archive: Wayback Machine URL<https://web.archive.org/web/20240822143451/https://skylandanalytics.net/skyland-pims-suite/>, retrieved on Aug. 22, 2024, URL<https://skylandanalytics.net/skyland-pims-suite/>, 6 pages.

* cited by examiner

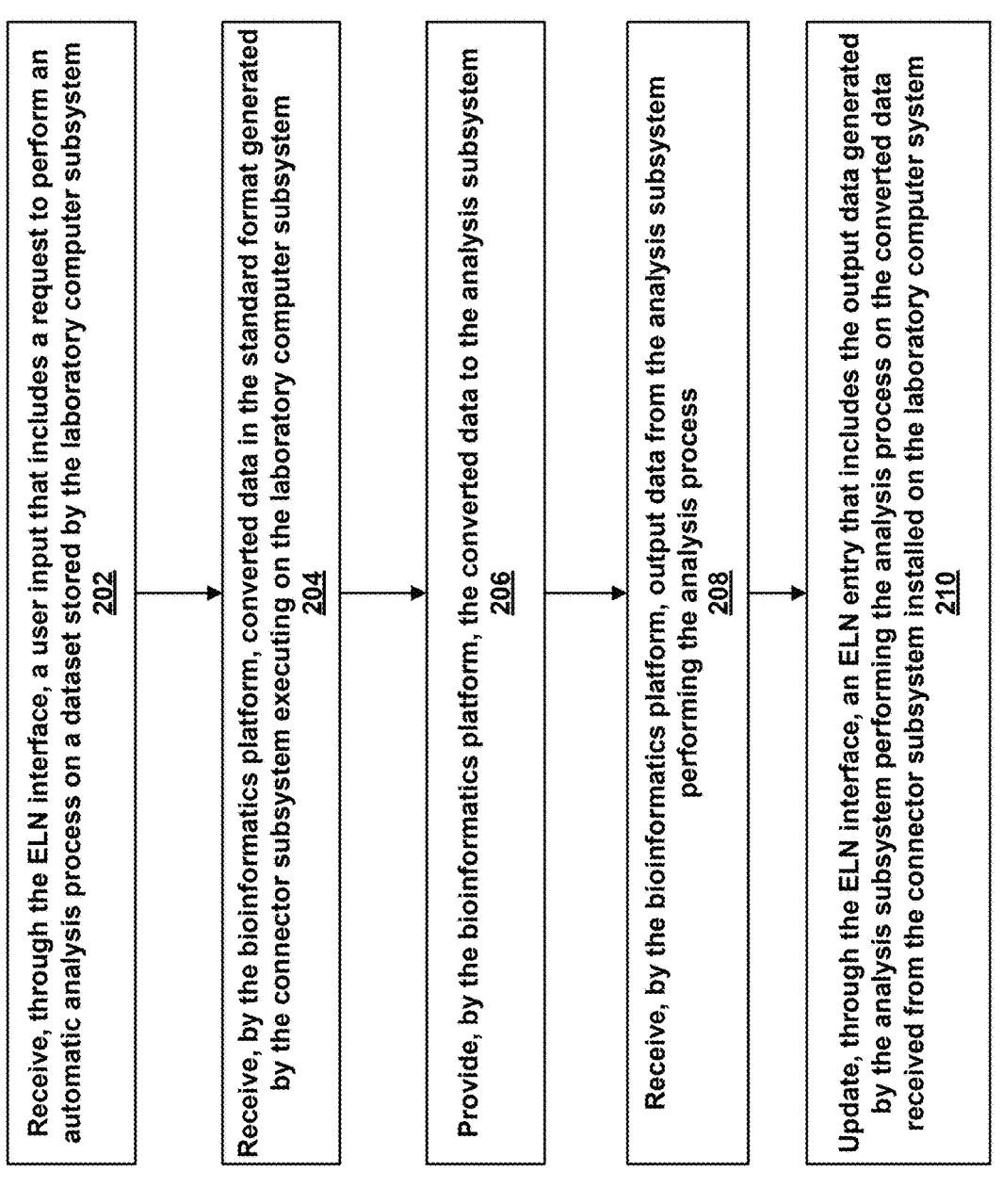

200

Receive, through the ELN interface, a user input that includes a request to perform an automatic analysis process on a dataset stored by the laboratory computer subsystem
202

Receive, by the bioinformatics platform, converted data in the standard format generated by the connector subsystem executing on the laboratory computer subsystem
204

Provide, by the bioinformatics platform, the converted data to the analysis subsystem
206

Receive, by the bioinformatics platform, output data from the analysis subsystem performing the analysis process
208

Update, through the ELN interface, an ELN entry that includes the output data generated by the analysis subsystem performing the analysis process on the converted data received from the connector subsystem installed on the laboratory computer system
210

Receive Converted Data
402

Determine Analysis Algorithm
404

Execute Analysis Algorithm
406

Generate Output Data
408

PLATFORM FOR END-TO-END BIOPROCESS OUTPUT DATA ANALYSIS

BACKGROUND

This specification relates to computing platforms for bioprocess output data analysis, where a bioprocess is a process that uses biological systems (e.g., cells, enzymes, solutions, etc.) to produce desired products (e.g., proteins, vaccines, biofuels, etc.), and where bioprocess output data is all recorded data collected associated with a bioprocess (during or after), i.e., any data related to the bioprocess, whether collected in real-time during the process, afterward, or both, and whether generated by the bioprocess device or another instrument.

This specification also relates to user interfaces. User interfaces (UI) can be used to display and interact with data maintained by cloud infrastructure, including servers, networks, and data storage devices. In particular, cloud infrastructure can support the uploading, maintaining, and editing of content on a user device using a UI configured with a data processing system that can store and access the appropriate data.

SUMMARY

This specification describes a platform system implemented as computer programs on one or more computers in one or more locations that receives user input that includes a request to perform an automatic analysis process on a dataset and ultimately updates a structured electronic laboratory notebook entry to include the output data & visualizations generated by the analysis.

Particular embodiments of the subject matter described in this specification can be implemented so as to realize one or more of the following advantages.

Life sciences products, including pharmaceuticals, vaccines, and chemical compounds, are typically developed in a bioprocess development cycle by a process development team using one or more process development facilities. The bioprocess development cycle may involve hundreds or thousands of experiments, trials, and data analyses and can take months or years of development, during which a synthesis or fermentation-based process for making the product, testing its quality and purity, and mixing with other substances to formulate a stable product, is iteratively modified.

The bioprocess development cycle may involve multiple scientists across different process development facilities. After the bioprocess has been developed and vetted, it may be productionized and produced at a production facility. Since the bioprocess development cycle is generally highly manual, can involve many different individuals and collaboration across different facilities, and can involve many different analyses of different types of bioprocess output data, the process is often disorganized and prone to errors. In particular, data analysis of bioprocess output data is often complicated by the need to source data from disparate sources that may not store the data in a standard format, and the manual analysis of the output data can be time-consuming and prone to errors.

This specification describes techniques that provide several improvements to the technological process of bioprocess development that address the aforementioned challenges. That is, the system improves the technological process of bioprocess development by providing an integrated technological solution to perform the analysis of bioprocess output data, such that analysis is automated, organized, error free, and can be performed at scale (i.e., for any number of bioprocesses output data, for any number of analyses) in real time. In addition, the system can standardize output data produced by bioprocess devices or other instruments for immediate data analysis or store the standardized data and provide it for future data analysis. And finally, the system can update an electronic laboratory notebook entry with analysis output data to support better decision making throughout the development process.

As a result, end-to-end bioprocess development can be greatly enhanced (in terms of accuracy and efficiency) while also being greatly accelerated.

For example, real-time end-to-end data analysis of bioprocess (e.g., cell culturing or biomolecule synthesis) output data (e.g., sensor measurements related to product yield) can be used to perform feedback-driven optimization of the respective bioprocess procedures (i.e., one or more unit operations, each parameterized by one or more material inputs, material outputs, steps, equipment, and bioprocess parameters). By having a closed loop feedback cycle to optimize the bioprocess, issues of manual procedures and human error can be avoided in the development life cycle.

Furthermore, the system's capability to perform automated analysis of bioprocess output data offers benefits to real-time study (i.e., immediate analysis of output data produced by single group) and cross-study (i.e., meta-analysis of output data associated with different groups). The system benefits real-time study because the system standardizes output data of a bioprocess (e.g., converting measurement units, using a standard file formatting, aligning timestamps, etc.) which enables the real-time end-to-end data analysis because inputs of an analysis are guaranteed to be in the correct and expected format upon generation. The system benefits cross-study because the system can standardize analysis output data into an expected, shared format that simplifies collaboration among teams. Thus, the system's standardized analysis output benefits meta-analysis of learnings across many studies from many groups, compounding the value of historical scientific experiments. As a particular example to illustrate the cross-study and real-time study benefits, consider a bioprocess of a reflux reaction to produce a bio-chemical product, where the bioprocess output data includes temperature per time point during the reaction, which can be in Fahrenheit at minute time points or Celsius at second time points. Having a standard format for the output data eliminates potential errors interpreting results across teams (a benefit to cross-study) and can simplify analysis workflow performed by computer programs by eliminating the need to format check inputs that are output data (a benefit to real-time study).

As another example of the benefits of the system, updating the electronic laboratory notebook entry with analysis output data enables users to make data-driven decisions in real-time to minimize errors. As a particular example, consider the bioprocess of reflux reaction to produce a bio-chemical product, where the reagents for the reaction are rare and are in limited supply. The real-time display of analysis output data can empower the user to terminate the bioprocess if the bioprocess is not proceeding as expected and will be wasteful of the reagents.

Furthermore, updating the electronic laboratory notebook entry with analysis output data also allows for automated data-driven decisions in real-time to minimize errors. For example, instead of a user manually reviewing the analysis output data, pre-defined criteria (e.g., a pre-configured termination criterion, e.g., environment temperature fluctuates outside of a pre-determined range) can be automatically applied to the analysis output data to trigger pre-defined decisions (e.g., ending the run of an assay and starting a new assay, and so on)

Another resulting benefit of the system's capability to perform automated analysis of bioprocess output data is that the system can be included in an automated instrument calibration process. For example, the system can be used to efficiently calibrate bioprocess devices or laboratory instruments without user intervention, thereby eliminating potential calibration errors and delays caused by manual user instrument calibration.

For example, instead of a user manually calibrating an instrument, an automated calibration procedure can iteratively adjust the instrument, automatically analyze outputs (using the system), and repeat the adjusting and the automatic analyzing until predefined calibration criteria are met. For example, using calibration standards (i.e., standardized inputs or samples for the instrument), a calibration procedure can calibrate an instrument until numerical outputs of the instrument matches the expected calibration standard numerical outputs to a pre-defined threshold to a degree a user cannot achieve.

As another example, a calibration procedure can include continuously monitoring instruments and, when predefined criteria regarding the outputs are satisfied, triggering a calibration procedure for the instrument. Examples of pre-defined criteria include automatically analyzing outputs (using the system) for issues (e.g., accuracy issues, output inconsistency, etc.) that exceed a pre-defined threshold and monitoring when conditions (e.g., instrument operating temperature) change beyond a pre-defined threshold. When the calibration procedure is triggered, automated calibration of the instrument, e.g., automated calibration of an instrument described previously above, can be executed. Thus, because the calibration procedure can operate continuously without interruptions, it eliminates delays associated with users deciding to and performing calibration.

Other improvements to the technologies of bioprocess development are described in commonly owned U.S. patent application Ser. No. 18/665,429, filed on May 15, 2024, entitled "COMPUTING PLATFORM FOR BIOPROCESS DESIGN, EXECUTION, ANALYSIS, AND TECHNOLOGY TRANSFER," as well as in commonly owned U.S. patent application Ser. No. 18/807,846, filed on Aug. 16, 2024, entitled, "BIOPROCESS EXECUTION WORKFLOW INTERFACES." The contents of these applications are herein incorporated by reference.

The details of one or more embodiments of the subject matter of this specification are set forth in the accompanying drawings and the description below.

Other features, aspects, and advantages of the subject matter will become apparent from the description, the drawings, and the claims.

DETAILED DESCRIPTION

Figure 1:
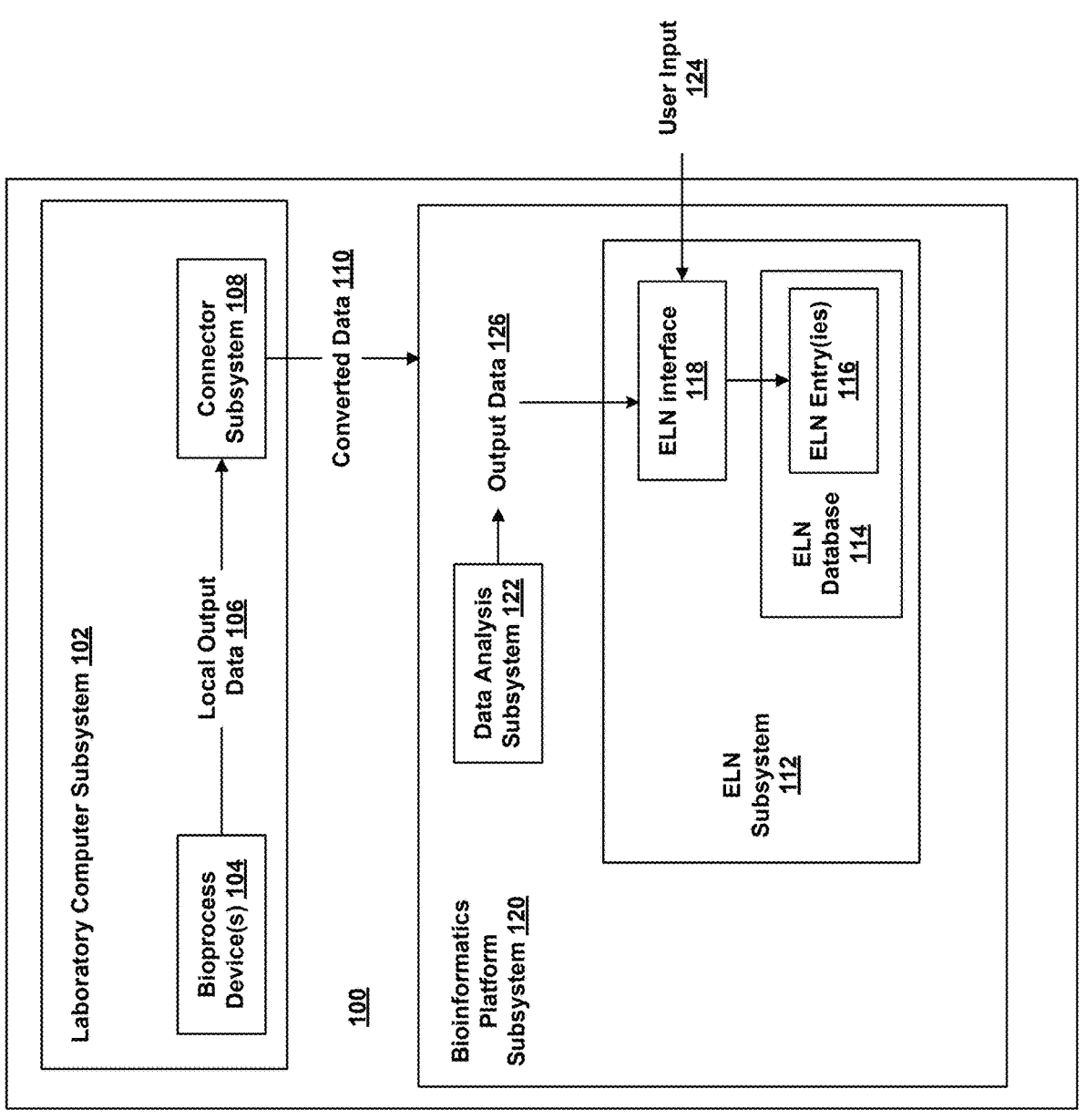
FIG. 1 shows an example platform system.

FIG. 1 shows an example platform system 100. The platform system 100 is an example of a system implemented as computer programs on one or more computers in one or more locations, in which the systems, components, and techniques described below can be implemented.

In particular, the system 100 receives a user input 124 that includes a request to perform an automatic analysis process on a dataset stored by a laboratory computer subsystem 102.

The request to perform an automatic analysis can include any of a variety of types of analyses. For example, the analysis can be statistical analysis, quality analysis, predictive modeling, data visualization (e.g., scatter plots, box plots, histograms, heatmaps, etc.), and so on.

For example, the request to perform an automatic analysis process can be to "generate a graph of the product yield curve over time for bioreaction data using <dataset>", where "<dataset>" indicates the file location or unique file identifier of a dataset stored by the laboratory computer subsystem 102.

The automatic analysis can also include multiple analyses, (e.g., evaluating data to determine properties, then performing statistical tests on the determined properties, then generating summary tables and summary visualizations of intermediate data).

As a particular example, the request to perform an automatic analysis process can be to "perform an Enzyme-Linked Immunosorbent Assay (ELISA) using data from microplate wells", where ELISA is a biochemical technique used to quantify (e.g., determine concentration) of species (e.g., proteins, antigens, hormones, small bio-molecules, and so on) in a sample (e.g., vial, or platted well) and the data from microplate wells (i.e., the dataset) includes light absorbance values of a plurality of samples. Included in the analysis can be the analyses of (i) generating a calibration curve to determine a relationship between absorbance at certain wavelength of light and predicted concentration of product of interest in a sample, (ii) predicting concentrations of product of interest in all samples, and (iii) statistically evaluating the reliability of the predictions.

Generally, the system 100 receives the user input 124 through an ELN (electronic laboratory notebook) interface 118.

The ELN interface 118 is part of an electronic lab notebook (ELN) subsystem 112 that maintains an ELN database 114 (e.g., cloud-based databases, on-premise databases, networked databases, etc.) storing a plurality of ELN entries 116 (i.e., digital record of laboratory notebook content, e.g., bioprocess output data, notes, videos, images, graphs, code, text, drawings, etc.). The ELN subsystem 112 can organize and store ELN entries 116 in an ELN database 114 that can be retrieved at any time (present or future). The ELN subsystem 112 can be implemented as a cloud-based application that provides a user interface (i.e., an ELN interface 118) for users.

The system 100 can present the ELN interface 118 to a user, e.g., by establishing a network connection with the end-user device. For example, the network can be a cloud-based network, the internet, or a local network.

In some implementations, for example, the ELN interface 118 is a computational notebook equipped interface for interactive data analysis that features "cells" that are text input areas where users can write, edit, and execute computer programming code or natural language text. The computational notebook equipped interface can interact with datasets from bioprocess devices in real-time. Additionally, the computational notebook equipped interface can include input fields (e.g., fields to specify dataset location, unique identifier for the dataset, a file upload field, data analysis parameters and so on), and the ELN interface 118 can include dropdown menus, search bars, and buttons to select tasks and analyses.

Generally, the system 100, in response to receiving the user input 124, begins the process of fulfilling the request to perform an automatic analysis process on a dataset by retrieving the dataset from the laboratory computer subsystem 102 where it is stored.

In some implementations, for example, the system 100 receives the user input 124 through the various fields, dropdown menus, search bars, "cells", etc. of the computational notebook equipped interface (i.e., the ELN interface 118) that specifies a dataset and a request to perform an automatic analysis process on the dataset and, in response, begins to fulfill the request to perform an automatic analysis process on the dataset.

In other words, the ELN interface 118 allows a user to simply and quickly being the automatic analysis process on a dataset stored by a laboratory computer subsystem 102 by submitting user input 124 to the system 100.

Generally, the dataset stored on the laboratory computer subsystem 102 is converted data 110 generated from local output data 106 from one or more bioprocess devices 104 or instruments included in the laboratory computer subsystem 102. For example, the laboratory computer subsystem 102 includes one or more bioprocess devices 104 configured to perform one or more respective bioprocess procedures and to generate local output data 106. And the laboratory computer subsystem 102 also includes a connector subsystem 108 configured to ingest the local output data 106, and to convert the output data 106 into a standard format (i.e., converted data 110).

In some cases, the generation of local output data 106 and conversion to converted data 110 happens in real-time. That is, the converted data 110 is generated and available as soon as the local output data 106 is generated and available.

Bioprocess device(s) 104 can be any appropriate laboratory equipment or instruments that can perform a bioprocess procedure and generates appropriate local output data 106, where a bioprocess procedure can be a recipe, and the recipe includes one or more unit operations, each parameterized by one or more material inputs, material outputs, steps, equipment, and bioprocess parameters.

Generally, the local output data 106 refers to any data related to the bioprocess, whether collected in real-time during the process, afterward, or both, and whether generated by the bioprocess device or another instrument.

For example, the bioprocess device 104 can be a bioreactor that performs the bioprocess procedure of product synthesis (e.g., ribosomal production of proteins) and that produces local output data 106 that includes product concentration (e.g., protein expression levels) per sample (i.e., bioreactor vessel that the protein production occurs in) during the bioprocess determined through the sensors of the bioprocess device.

As another example, the bioprocess device 104 can again be a bioreactor that performs the bioprocess procedure of product synthesis (e.g., ribosomal production of proteins) to produce a product sample, but the local output data 106 can this time be light absorbance spectrum of the product sample taken by a light spectrometer that measures light matter interaction of a sample (e.g., absorbance, scattering, etc. of a substance or solution) after the bioprocess has completed.

As another example, the bioprocess device 104 can be a chromatography system that performs the bioprocess procedure of product separation (e.g., protein separation) and that produces local output data 106 that includes fraction volumes, content, and content concentrations.

Generally, the conversion of local output data 106 to a standard format to generate converted data 110 includes numerical transformations, unit conversions, mapping to pre-defined file formats, and so on.

For example, consider local output data 106 from a spectrometer that exports light intensity per wavelength at various second timepoints of a sample in a CSV formatted file throughout a time period. The system 100 can perform spectral subtraction (i.e., subtract a constant scalar from each numerical input as a numerical transformation) to account for spectral contributions of known components. The system 100 can also convert the units of wavelength to frequency (i.e., perform unit conversion). The system 100 can also convert the CSV file format to Hierarchical Data Format (HDF), e.g., HDF4, HDF5, or to Python Pandas DataFrame file (i.e., map to pre-defined file formats).

By standardizing data (i.e. converting local output data 106 to a standard format to generate converted data 110), the system 100 simplifies automatic analysis by guaranteeing consistency of data format, units, and preprocessing. In turn, the automatic analysis process is simplified, and reproducible for multiple collaborating users analyzing the same dataset.

Further details of generating converted data are described below with reference to FIG. 2 and FIG. 3.

The system 100 receives, by a bioinformatics platform 120, converted data 110 in the standard format generated by the connector subsystem 108 executing on the laboratory computer subsystem 102. The bioinformatics platform subsystem 120 maintains a data analysis subsystem 122 for performing automatic analysis processes on one or more bioprocess datasets.

In some cases, the data analysis subsystem 122 can receive data from external biological databases or chemical databases to perform an automatic analysis. For example, the data analysis subsystem can retrieve NMR (nuclear magnetic resonance) spectrum from a chemical database to perform a chemical identification analysis on experimental NMR spectrums.

The system 100 can receive, by a bioinformatics platform 120, the converted data 110 through any of a variety of means, e.g., through a network connection, e.g., a cloud-based network, the internet, or a local network. For example, an internet network connection can facilitate the bioinformatics platform 120 receiving the converted data 110 through an API call. Also, for a network connection that is a local area network connection to a database, e.g., a SQL database, the bioinformatics platform 120 can receive the converted data 110 through a query, e.g., a SQL database query. Similarly, a network connection to a shared filed system (i.e., a shared file system that allows multiple users or devices to access and manage files or memory concurrently over a network) can facilitate the bioinformatics platform 120 receiving the converted data 110 through a file sharing protocol (e.g., file transfer protocol).

The system 100 provides, by the bioinformatics platform 120, the converted data 110 to the analysis subsystem 122.

The system 100 uses the analysis subsystem 122 to process converted data 110 to generate output data 126 (i.e., analysis output data) through advance analysis algorithms.

For example, the analysis subsystem 122 can perform curve fitting, statistical tests, or machine learning (ML) (e.g., developing a ML model, performing inference with a ML model, using inference results for a downstream task, and so on).

Further details of performing automatic analysis processes on one or more bioprocess datasets are described below with reference to FIG. 2 and FIG. 4.

The system 100 receives, by the bioinformatics platform 120, output data 126 from the data analysis subsystem 122 performing the analysis process.

The system 100 can receive, by a bioinformatics platform 120, the output data 126 through any of a variety of means, e.g., through a network connection, e.g., a cloud-based network, the internet, or a local network.

For example, the system 100 can receive the output data 126 in response to a programming function call transmitted over a network connection.

The system 100 updates, through the ELN interface 118, an ELN entry 116 that includes the output data 126 generated by the analysis subsystem 122 performing the analysis process on the converted data 110 received from the connector subsystem 108 installed on the laboratory computer system 102.

The system 100 can attach the analysis output to an ELN entry that can be displayed to one or more users, saved for record keeping and accessed at any time (present or later), or further manipulated or added to by one or more users.

In some cases, the system 100 is further configured to evaluate the output data 126 from the analysis subsystem performing the analysis process on the one or more bioprocess datasets to perform feedback-driven optimization of the respective bioprocess procedures of the bioprocess datasets.

For example, the system 100 can evaluate output data 126 that includes information of product yield of a bioprocess. Then the system can modify the recipe of the bioprocess (i.e., modify one or more unit operations, one or more material inputs, steps, equipment, bioprocess parameters etc.) to attempt to have the bioprocess produce a greater yield. After generating new output data and evaluating if the yield was greater, the system can perform another modification of the bioprocess and generate new output data, and so on, until the product yield for the bioprocess has been maximized.

Figures 1, 5:
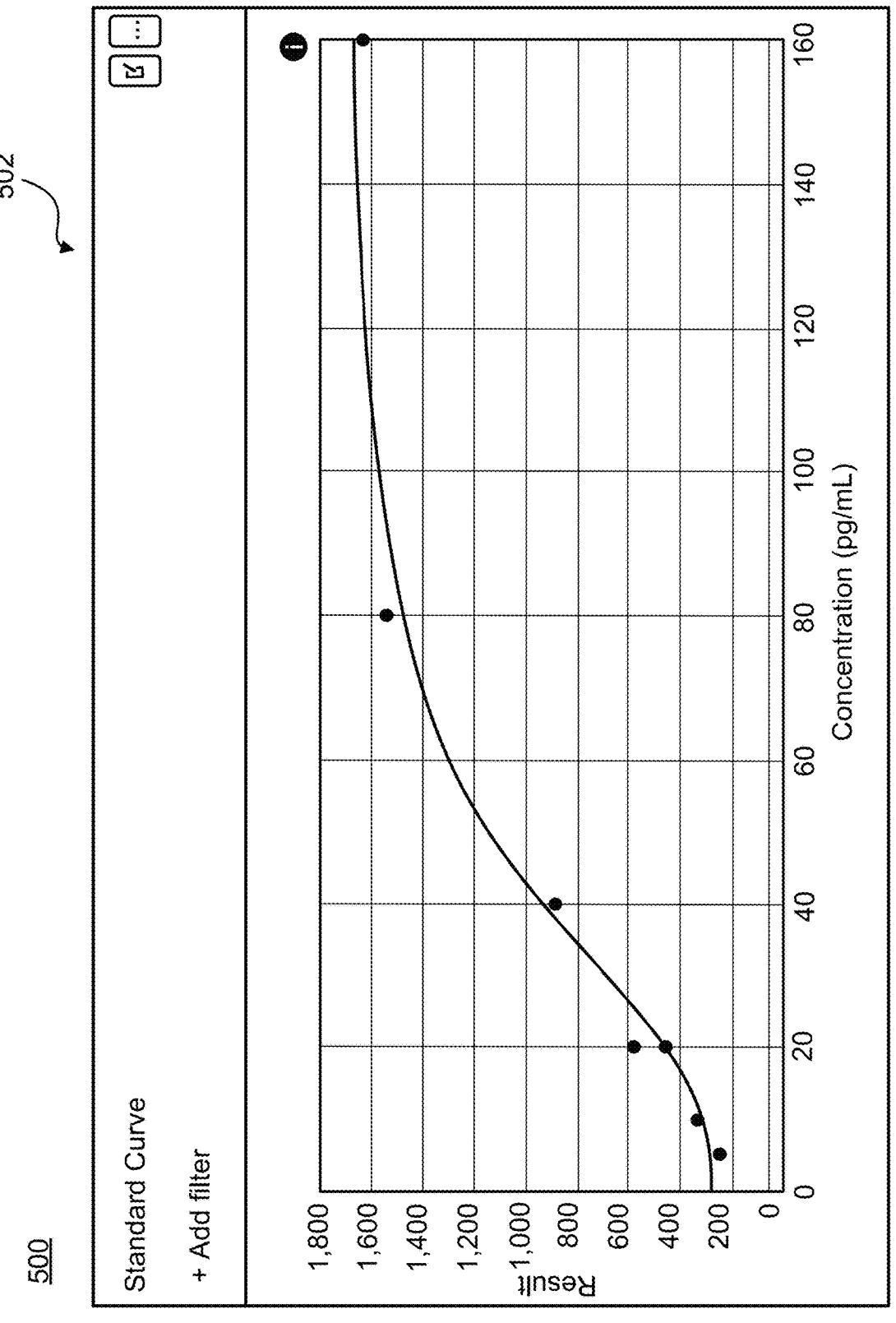
FIG. 5 shows an example electronic laboratory notebook interface display of an electronic laboratory notebook entry.
Figures 2, 5:
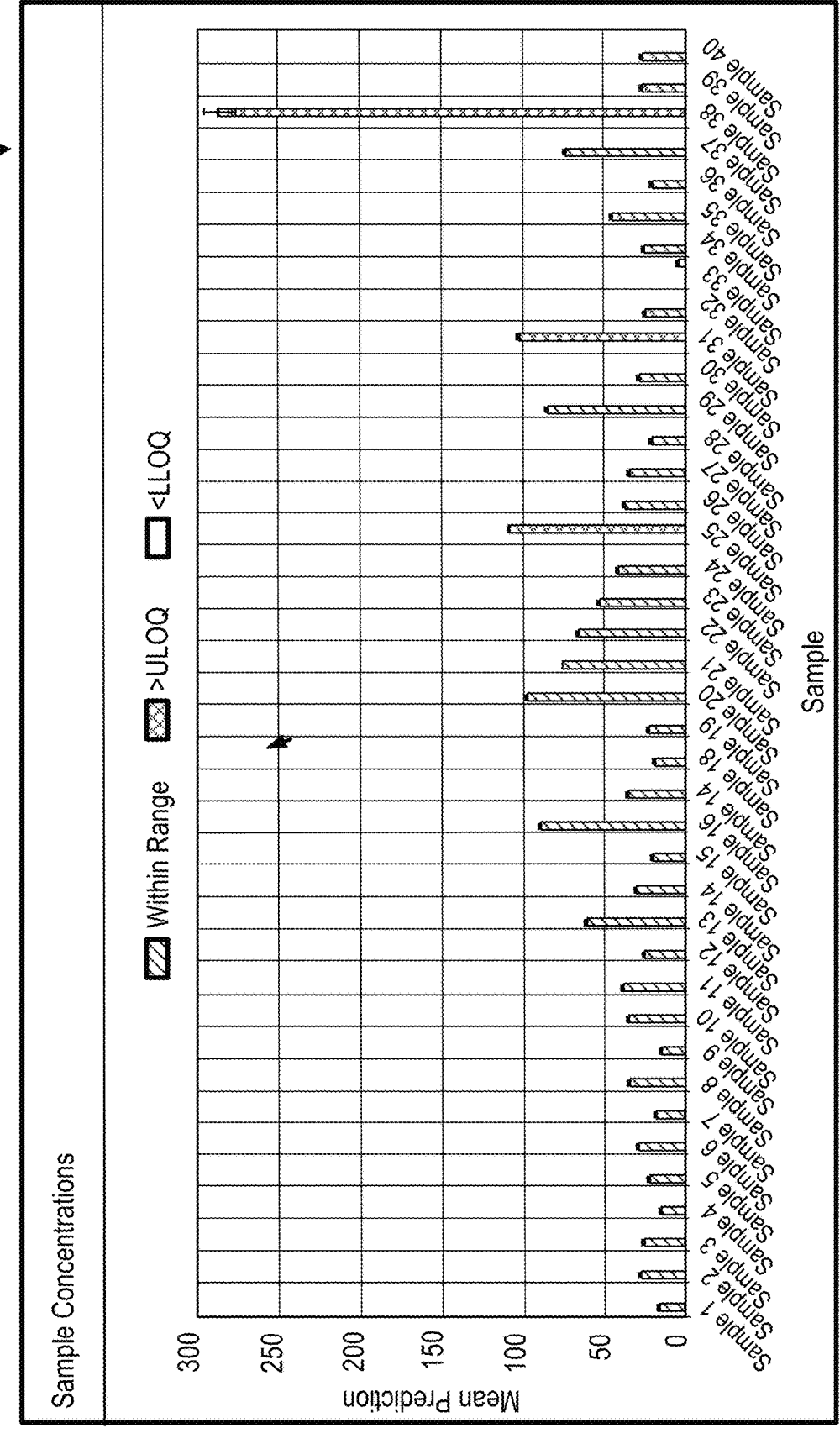
FIG. 2 is a flow diagram of an example process for performing end-to-end data analysis.
Figures 3, 5:
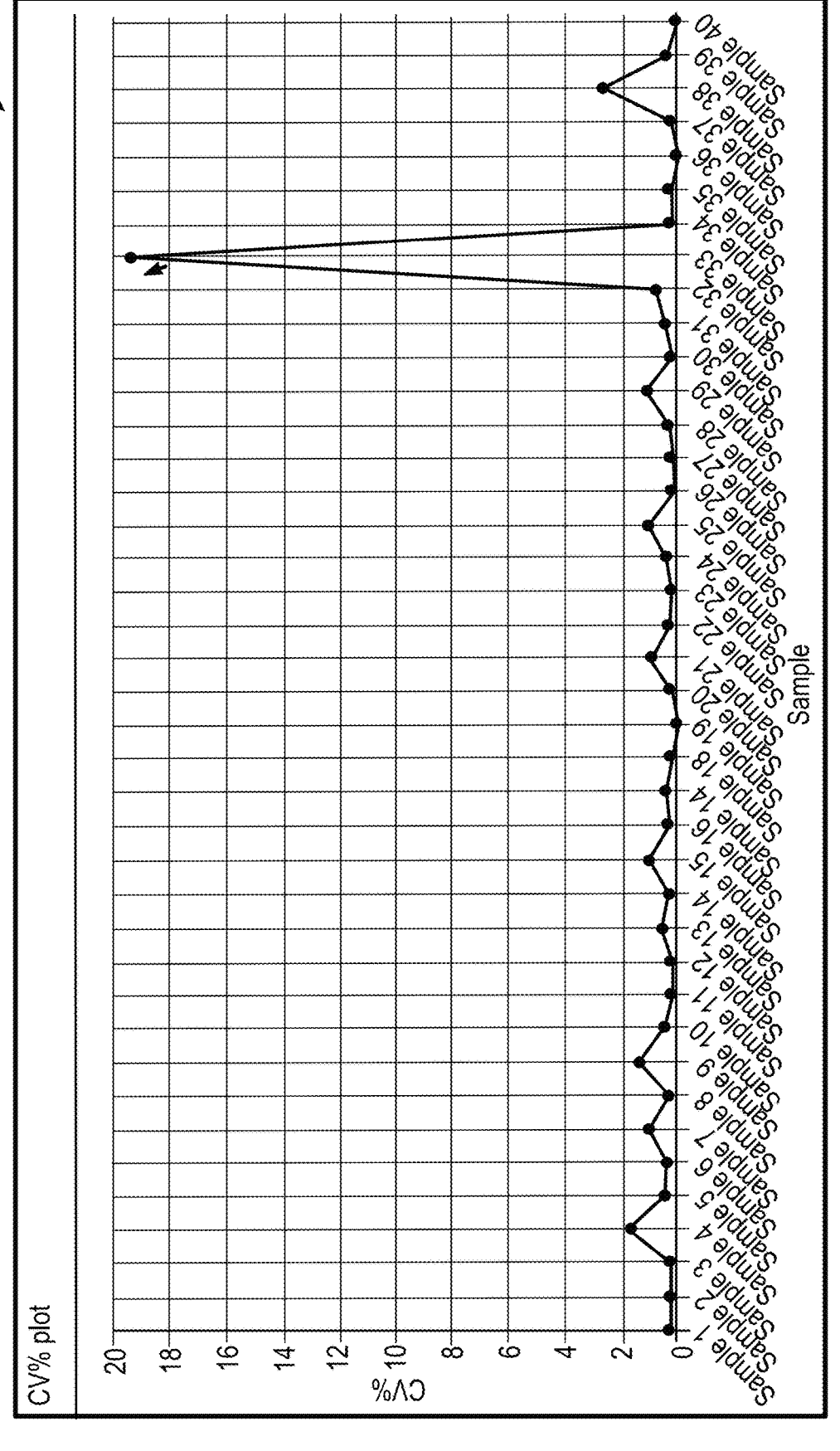

FIG. 2 is a flow diagram of an example process 200 to perform end-to-end data analysis. For convenience, the process 200 will be described as being performed by a system of one or more computers located in one or more locations. For example, a platform system, e.g., the platform system 100 of FIG. 1, appropriately programmed in accordance with this specification, can perform the process 200.

The system receives, through the ELN interface, a user input that includes a request to perform an automatic analysis process on a dataset stored by the laboratory computer subsystem (step 202).

As described above, the request to perform an automatic analysis can include any of a variety of types of analysis. For example, the analysis can be statistical analysis, quality analysis, predictive modeling, data visualization (e.g., scatter plots, box plots, histograms, heatmaps, etc.), and so on.

The automatic analysis can include data structuring and insight extraction. For example, the automatic analysis can be to create a table of product growth rates across multiple samples. Or the automatic analysis can be to graph the product growth rate of multiple samples over time. As another particular example, the automatic analysis can be to identify data points in data that are outliers using statistical tests. Then to return a list of sample IDs along with the statistic used to determine the sample's data's outlier status.

The automatic analysis can include the use or development of machine learning models. For example, the automatic analysis can be to use a pre-trained machine learning model to predict product quality of various samples based on sample characteristics. For example, a supervised machine learning model (e.g., neural network, tree-based models, logistic-regression model, etc.) pre-trained on historical bioprocess data with known sample quality and sample characteristics can be used to predict the sample quality of samples included in a dataset. As another particular example, the automatic analysis can be to train a machine learning model, e.g., train the ML of type described in the previous example using data that is historical bioprocess data.

As another particular example, the automatic analysis can be to perform ELISA on data that includes a number of product samples to quantify the presence of a specific biomolecules in the product samples.

As described above, in some cases, the request to perform an automatic analysis can include multiple analyses.

For example, the automatic analysis can be to perform ELISA such that it includes (i) determining a relationship between optical absorbance and biomolecule quantity for standard samples (i.e., samples with known biomolecule quantities), (ii) generate a graph of the relationship, (iii) use the relationship to infer biomolecule quantity for samples with unknown biomolecule quantities, and (iv) statistically evaluate the reliability of each sample inference.

An advantage of including multiple analyses in one analysis is the elimination of the need to switch between multiple software or tools perform the analyses. Additionally, the analysis is streamlined.

The ELN interface can be any of a variety of interfaces that can receive user requests, can receive output data from a data analysis subsystem, can send user requests to a bioinformatics platform subsystem, and can update an ELN entry that includes the output data from a data analysis subsystem. Generally, the ELN interface allows a user to view and interact with the coupled ELN entries the ELN interface can communicate with.

An ELN entry generally is an electronic record that one or more users can access, and, in some cases, user access is restricted according to platform security protocols. The ELN entry can include laboratory protocols, data, data analysis outputs (e.g., graphs, predictions, identifications, and so on), images, videos, code, text, links, etc.

In some cases, the user input includes a request to create an ELN entry. In other cases, the user input includes a request to access a pre-existing ELN entry.

The ELN interface can be, for example, a web-based or software-based interface (accessed on a computer, a tablet, a smart phone, or any other appropriate end-user device), where a user can interact with the interface through typing, clicking, dragging, touching, voice command, or any other appropriate interaction.

As another example, the ELN interface can be a command line terminal, where the user can send inputs through typed commands and receive output as terminal display output.

As another example, as described above, the ELN interface can be a computational notebook equipped interface for interactive data analysis that features "cells" that are text input areas where users can write, edit, and execute computer programming code or natural language text. The computational notebook equipped interface can interact with datasets from bioprocess devices in real-time.

In some implementations, after the system receives a user input, the ELN interface can prompt the user to provide further inputs, such as selection of bioprocess datasets, specification of analysis type, additional custom parameters, and so on.

For example, the system can prompt the user with drop-down menus or buttons for selecting types of analysis after the system receives a user input.

As another example, the user can be prompted to select components of the automatic analysis process, where the process is a series of steps performed one after the other, and the steps are modular and can be customized, added, or removed to the entire analysis process.

As a particular example, the system can receive a user input via an ELN interface that includes executed code in a "cell" of a computational notebook equipped interface. Then the system can prompt the user for a specific dataset through a pop-up field. Then the system can prompt the user for a specific analysis workflow through a drop-down menu.

In some cases, the electronic laboratory notebook subsystem is configured to have security features that includes restricting the request to perform an automatic analysis process on a dataset stored by the laboratory computer subsystem that can be received by a user based on the user security level.

For example, if a user does not have the appropriate user security level, then a request to perform an automatic analysis process on a dataset can be denied. For example, the system can decline to retrieve the dataset, decline to perform the automatic analysis, or both.

The system receives, by the bioinformatics platform, converted data in the standard format generated by the connector subsystem executing on the laboratory computer subsystem (step 204).

As described above and will be described in more detail below, the converted data is generally local output data (i.e., any data related to the bioprocess produced by the biopro-cess device or another instrument) converted to a standard format through any of a variety of transformations, e.g., numerical transformations, unit conversions, mapping to pre-defined file formats, and so on.

Further details of generating converted data are described below with reference to FIG. 3.

The system provides, by the bioinformatics platform, the converted data to the analysis subsystem (step 206) so that the analysis subsystem can perform automatic analysis pro-cesses on the converted data (i.e., one or more bioprocess datasets).

The system can use the analysis subsystem, after receiv-ing converted data, to process the converted data through a sequence of steps.

The system first determines the analysis algorithm based on the user input, the converted data, or both. For example, the user input can include information of, in addition to which bioprocess datasets to perform analysis on, the type of analysis to perform on the dataset. Then the system can process the user input, any accompanying parameters for the analysis that might be included in the user input, and the converted data to determine the analysis algorithm.

In some cases, the user input specifies the analysis and any necessary parameters for the analysis.

In some cases, a user can create a custom automatic analysis and the system can store and use the custom automatic analysis. For example, the user input can specify a new custom analysis that the system will store, or the user input can specify a previously created custom analysis.

For example, the user input can specify that converted data "growth_data_20241120.csv" (which contain data of cell count at various timepoints) from the bioreactor bio-process will be analyzed through a graphing analysis (i.e., display a graph of the cell count growth curve) with a parameter that specifies "smoothing the curve with a moving average window of 3 timepoints".

As another example, the user input can specify that converted data "protein_expression_data_20241120.pkl" from the bioreactor bioprocess will be analyzed through a protein expression analysis (i.e., determine which samples have protein expression that deviate significantly from a baseline expression) with parameters that specifies "use the 't-test' statistical test with a p-value of 0.05 for each sample".

In some cases, the user input does not specify an explicit automatic analysis, but instead, the system determines a default analysis based on the converted data.

For example, when the user input does not specify an analysis the system can process metadata associated with the converted data, e.g., metadata specifying the bioprocess device or instrument that produced the data, to determine a default type of analysis to perform.

For example, if the converted data "sample_ab123.mzXML" contains metadata (e.g., one or more tags, e.g., natural language tags or coding tags) that indicate it is the output data of a mass spectrometer that processed a biochemical sample (data that includes the relative abundance of chemical species of various mass to charge ratios), the system can determine the default analysis to be to identify the chemical species of the top 10 most abundant mass to charge ratios.

The system then executes the analysis algorithm to gen-erate the output data, which can be, e.g., executing a computer script, curve fitting, performing statistical tests, performing machine learning processes, etc.

In particular, in some cases, a system can perform the execution of the analysis algorithm in parallel. For example, the system can use a plurality of parallel processing devices, e.g., CPUs, GPUs, TPUs, or other ASICs, FPGAs, and so on, to perform the execution of the analysis algorithm in par-allel.

As a particular example, the system can deploy multiple instances of a pre-trained neural network across devices. For example, the system can deploy each instance on a different device or deploy an instance across multiple devices using model parallelism techniques. Then the system can execute the neural network in parallel across devices.

As another particular example, the system can execute the statistical analysis of dataset across multiple devices executed in parallel by distributing converted data across devices for processing.

An advantage of the system executing analysis in parallel, in addition to latency improvements and scaling improve-ments for the analysis, is that it abstracts the complexities of parallel computing from users, allowing the users to benefit from its efficiency without requiring expertise in parallel computing.

The output data of the analysis can be graphs, tables, processed data, statistical quantities, etc.

Further details of performing automatic analysis pro-cesses on one or more bioprocess datasets are described below with reference to FIG. 4.

The system receives, by the bioinformatics platform, output data from the analysis subsystem performing the analysis process (step 208).

The system updates, through the ELN interface, an ELN entry that includes the output data generated by the analysis subsystem performing the analysis process on the converted data received from the connector subsystem installed on the laboratory computer system (step 210).

In other words, the output data of the analysis (e.g., graphs, tables, processed data, statistical quantities, and so on) can be integrated into the relevant ELN entry for one or more users to access. Having the output data of the analysis in an ELN for one or more users to access, helps foster collaborative insights.

In some cases, steps 204-210 are performed in real-time repeatedly. That is, the bioinformatics platform is configured to perform operations in real-time such that as local output data associated with a bioprocess is generated in real time, the system executes steps 204-210 on the presently available local output data and continues to repeat steps 204-210 until the generation of new local output data ends or the user intervenes.

Figure 3:
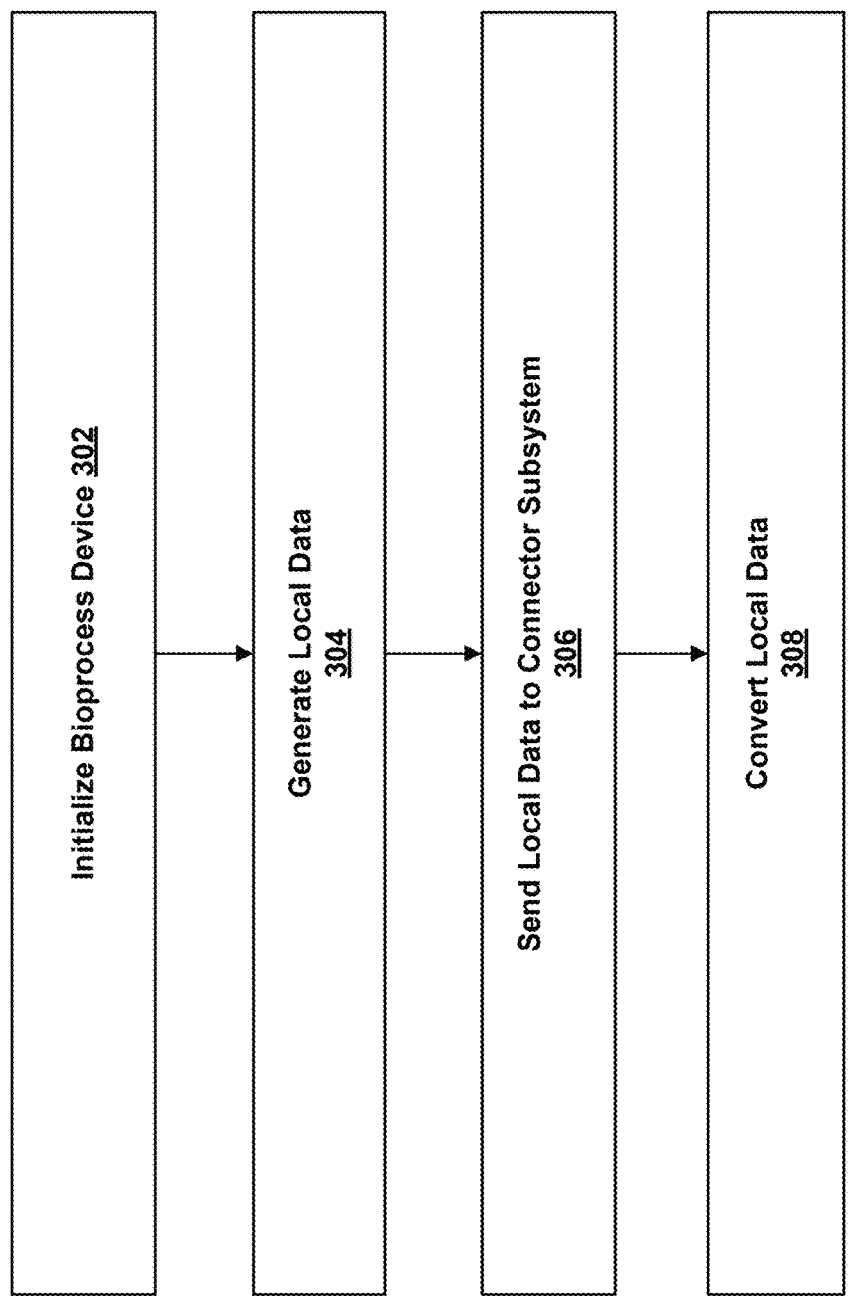
FIG. 3 is a flow diagram of an example process for generating converted data.

FIG. 3 is a flow diagram of an example process 300 for generating converted data. For convenience, the process 300 will be described as being performed by a system of one or more computers located in one or more locations. For example, a platform system, e.g., the platform system 100 of FIG. 1, appropriately programmed in accordance with this specification, can perform the process 300.

Although the example process 300 provides details of one bioprocess generating converted data, it should be understood that this process is not limited to a single bioprocess. Instead, it is an example of a single bioprocess generating converted data in a set of one or more bioprocesses generating converted data (e.g., the one or more bioprocess devices 104 of FIG. 1 performing one or more bioprocesses).

The system initializes the bioprocess device (302). For example, the system can configure the bioprocess device, ensure that the bioprocess device is calibrated (i.e., the device sensors have been verified and or adjusted to provide accurate data), operational (i.e., all device components are functioning appropriately), and ready for operation (i.e., the system is available to perform the requested bioprocess procedure, and the configuration parameters for the bioprocess procedure is valid).

For example, to ensure the bioprocess device is calibrated, the sensors readings can be compared to a known standards and the bioprocess device settings can be adjusted according to the comparison.

As a particular example, a mass spectrometry device can process a known standard sample to produce a mass spectrometry spectrum (relative abundances of mass to charge ratios). Then the mass spectrometry device can adjust the mass spectrometry device settings to account for any discrepancy between the mass spectrometry spectrum sample reading and the expectation for the sample.

As another example, to ensure the bioprocess device is operational the device can run a diagnostic test on each of its components to validate that the components work.

As a particular example, a bioreactor device can run a diagnostic test of its temperature control component by heating a solvent to particular temperatures, and then cooling the solvent to particular temperatures to check that the temperature control component can reach each of these checkpoints.

As another example, to check that the bioprocess device is ready for operation, the system can check if the configuration parameters are valid (i.e., will not cause damage to the device or are consistent with the devices capabilities)

As a particular example, the parameter configuration for a reflux reaction might have a set temperature for the heating mantle that exceeds the max temperature the heating mantle can achieve. The system, checks the parameter configuration, determines that the temperature setting is not valid and terminates the bioprocess procedure. Then notifies the user that the request cannot be fulfilled and why.

The system's bioprocess device or any other related instrument generates local data (step 304). For example, the bioprocess device can begin its respective bioprocess procedure and can begin generating data through real-time measurements from sensors or through another instrument.

For example, a bioprocess device may be a bioreactor performing the bioprocess procedure of growing a cell culture. In which case, the bioprocess device can generate local data such as temperature reading, light absorbance spectrum of the reactor vessel, pH reading every second, minute, or hour.

As another example, a related instrument to the bioprocess may include a mass spectrometer. In which case, the mass spectrometer can generate local data such as the mass spectrum (i.e., the mass to charge ratios of the ions present in a sample plotted against their intensities).

As another example, a related instrument to the bioprocess may be a microplate reader. In which case, the microplate reader can generate local data such as absorbance of light per platted well of a microplate.

The system sends the local output data to the connector subsystem (306).

In some cases, the system includes metadata (i.e., additional data beyond those recorded by the device sensors or instrument that describe the data) in the local output data before sending the local output data to the connector subsystem. The metadata can include, e.g., bioprocess device or instrument type, bioprocess device or instrument ID, sensor type, time that data was collected, state of device, experiment name, sample ID, bioprocess user initiator, and so on.

The system can send the local output data to the connector subsystem through any of a variety of means, e.g., a network connection, e.g., cloud-based network, the internet, or a local network. As a particular example the system can send the local output data through API calls.

The system converts the local data into standard format (step 308).

As described above, the conversion of local output data to a standard format to generate converted data includes numerical transformations, unit conversions, mapping to pre-defined file formats, and so on. The goal of the conversion is to create converted data that is suitable for further analysis, integration with other systems, or convenient to share with multiple users.

For example, local output data that includes a growth curve (e.g., cell count at particular timepoints) can be converted to a derivative growth curve (through the numerical transformation of finite differences of time series points) so that analysis of dynamics of product growth can be analyzed.

As another example, local output data that includes a bioreactor's readings of temperature in Fahrenheit can be converted to Kelvin (through unit conversion) to adhere to the standard of the international system of units.

As another example, local data in a propriety device format that includes a bioprocess device's measurements of gas concentrations (e.g., carbon dioxide concentration, oxygen concentration, and so on) can be converted to a CSV format (through a mapping to the pre-defined file format) for compatibility with downstream analysis software or computer programs.

Although each of the previous examples may describe one transformation on a subset of data (e.g., a single numerical transformation of one sensor reading type) the system may perform one or more transformations on any number of subsets of local output data. For example, the system can perform a numerical transformation and then a unit conversions on the same subset of data; the system can perform one or more different numerical transformations on one or more subsets of data; the system can perform unit conversation of a subset of data followed by one or more numerical transformation of subsets of data, and then map the final transformed data to a pre-defined file format.

An advantage of converting data to standard format includes ensuring compatibility across different systems and analyses.

Figure 4:
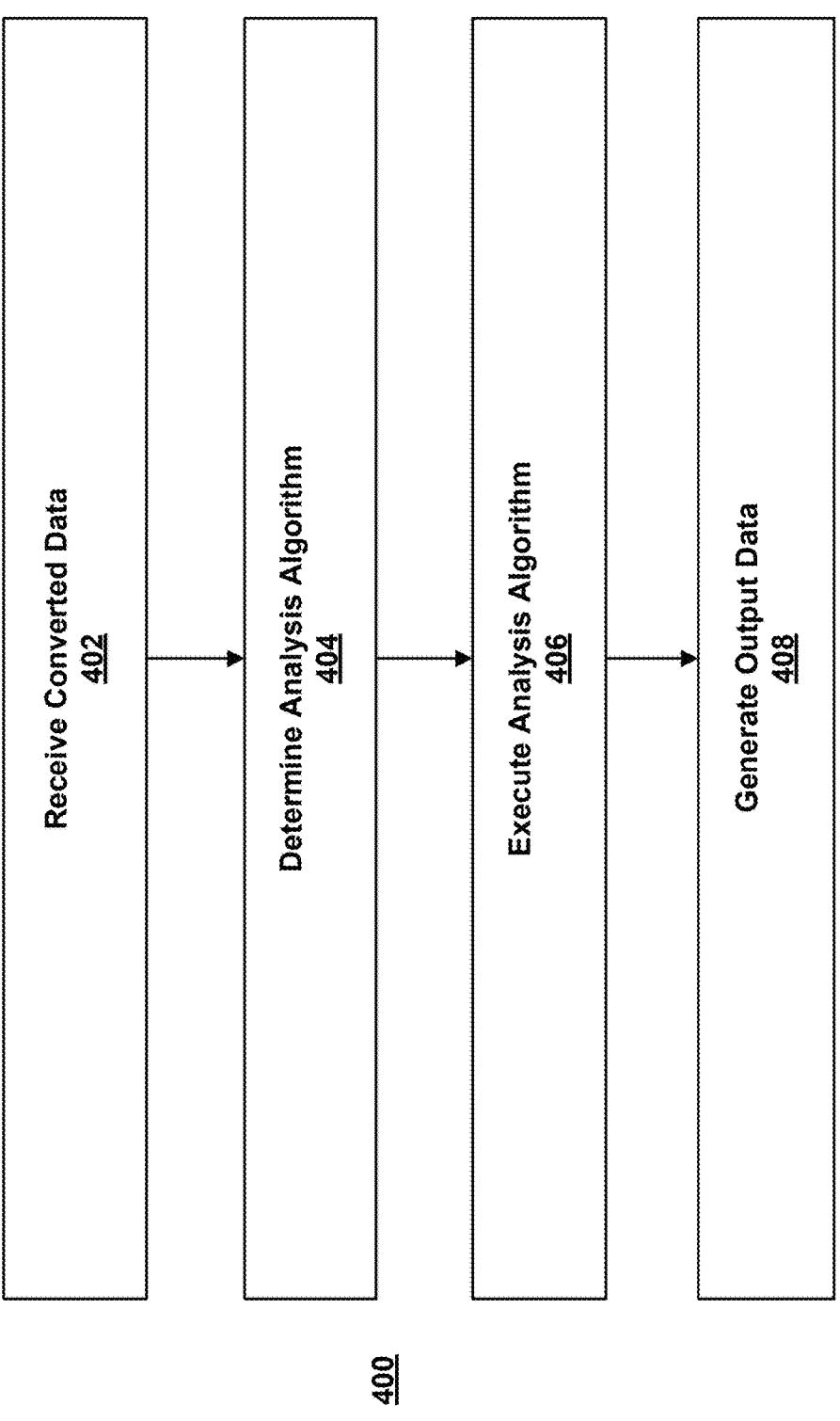
FIG. 4 is a flow diagram of an example process for performing automatic analysis.

FIG. 4 is a flow diagram of an example process 400 for performing automatic analysis. For convenience, the process 400 will be described as being performed by a system of one or more computers located in one or more locations. For example, a platform system, e.g., the platform system 100 of FIG. 1, appropriately programmed in accordance with this specification, can perform the process 400.

The system receives converted data from the connector subsystem (step 402).

After receiving the converted data, the system determines an analysis algorithm (step 404) based on the converted data, the user input, or both.

Generally, the system determines the analysis algorithm using the user input. In other words, the user input can include all information necessary to determine the analysis.

In some cases, the user input can identify an explicit algorithm to perform on converted data. For example, the user input can include parameters or selections or other information that specify the system should "apply linear regression to analyze the correlation between temperature and bioreaction product yield."

In some cases, the user input can include all relevant parameters associated with an explicit algorithm, in addition to the specification of an explicit algorithm. For example, the user input can include parameters or selections or other information that specify the explicit algorithm is to "train a ML classifier" and the relevant parameters to the explicit algorithm can be, e.g., "ML model type" (e.g., Gradient boosting trees), "max_depth" (i.e., a hyperparameter associated with gradient boosting tree models), "max_trees" (i.e., a hyperparameter associated with gradient boosting tree models).

In some cases, the user input specifies an analysis algorithm that is a composition of several analysis algorithms. For example, the user input can specify an automatic analysis that includes (i) "graph scatter plot of data", (ii) "perform linear regression", and (iii) "identify outliers" as "first graph a scatter plot of data, then perform linear regression on the scatter plot points, and then identify outliers in the graph."

In some cases, the system determines the analysis algorithm using the metadata included in the converted data. For example, the system can automatically select the most appropriate analysis procedure based on specific characteristics present in the metadata.

For example, the system can determine the analysis algorithm based on metadata by evaluating hierarchical criteria. For example, the system can process metadata to determine the unique identifier of the bioprocess device or instrument that generated the data and the type of bioprocess device or instrument. Then the system can determine the analysis to be that associated with the identifier. But if the system does not maintain an analysis algorithm associated with the identifier, then the system determines the analysis to be that associated with the type. But if the system cannot determine an analysis associated with the type, then the system determines the analysis to be that associated with the next metadata item in the hierarchy. In this way, the system can progress through a hierarchy of criteria until a criterion is reach that can be satisfied, the final criterion being that if no data in the metadata is associated with an analysis then the analysis algorithm is "identity" (i.e., only to load data).

As described above, in some cases, the user input can specify a new custom analysis that the system will store and use, or the user input can specify a previously created custom analysis that the system will use.

Once the system determines the analysis algorithm, the system executes the analysis algorithm (step 406).

As described above, in some cases the system can execute the analysis algorithm in parallel. For example, the system can use a plurality of parallel processing devices, e.g., CPUs, GPUs, TPUs, or other ASICs, FPGAs, and so on, to perform the execution of the analysis algorithm in parallel.

In some cases, the system can display the progress of the analysis algorithm to the user through the user interface. For example, the system can display a progress bar, or intermediate outputs (e.g., graphs, tables, etc.) to the user as the analysis algorithm executes.

After executing the analysis algorithm, the system generates the output data of the analysis (step 408), which are the results of the analysis algorithm execution. These outputs can include, e.g., data, statistical reports, graphs, visualizations, tables, predictions, etc.

FIG. 5 illustrates an example 500 electronic laboratory notebook interface display of an electronic laboratory notebook entry. As an example, the platform system 100 can provide the example 500 electronic laboratory notebook interface display to an end-user device.

In particular, the example 500 display of an entry includes three elements, i.e., an example 502 curve fit to standard samples, an example 504 bar chart plot of predicted concentrations of samples, and an example 506 of visualizing the coefficient of variation (CV %) through a scatter line plot for the predicted concentrations of samples.

The three elements (i.e., 502, 504, and 506) are the result of a user input that includes a request for the automatic analysis to perform ELISA on converted data such that it includes (i) determining and plotting the relationship between optical absorbance and biomolecule concentration for standard samples (i.e., example 502), (ii) using the relationship to infer biomolecule concentration for samples with unknown biomolecule quantities and creating bar chart plot of these inferences (i.e., example 504), and (iii) visualizing the CV % of each sample inference (i.e., example 506).

In other words, for this particular example 500, the system, through an ELN interface (e.g., a "notebook-like environment") received a user input (e.g., executed code in a cell of a "notebook-like environment" that subsequently prompted the user for information regarding a dataset and the type of automatic analysis requested) that included a request to perform an automatic analysis that results in output data (i.e., example 502, example 504, example 506) that was then incorporated into an updated ELN entry through an ELN interface.

In particular, for the generation of the example 502 curve fit to standard samples, the automatic analysis included (i)

the system determining a mathematical model (e.g., logistic model, linear model, etc.) that fits the data of standard samples (i.e., the scatter plot of metabolite concentration in sample vs light absorbance of sample) using a criterion (e.g., selecting the model with the highest coefficient of determination). Then the system (ii) generating a plot of the data of standard samples along with the fitted mathematical model.

For the generation of the example 504 bar chart plot of predicted concentrations of samples, the automatic analysis can include the system applying the fitted model to the replicate light absorbance data of unknown samples to determine the concentrations of these unknown samples. For example, the system can apply the fitted mathematical model of example 502 to the replicate light absorbance readings (i.e., multiple light absorbance reading for each sample) to generate predicted concentration values for each sample. Then the system averages the predicted concentration values of the replicates for each sample, and generates a visualization of the averages through a bar plot.

Finally, for the generation of the example 506 of visualizing the coefficient of variation (CV %) through a scatter line plot for the predicted concentrations of samples, the automatic analysis included the system, for each sample, computing the standard deviation of the predicted concentration values of replicates and then dividing the standard deviation by the mean and multiplying the result by 100 to generate the CV %. Then the system generating a line scatter plot of the CV % of each sample.

The system performing an automatic analysis that results in the example 500 display of an entry that includes examples 502, 504, and 506 eliminates manual calculations, reduces human error, streamlines analysis workflow, and ensures reproducible results for data analysis.

While described here within the context of bioprocess control, the system of this specification can be applied within the context of other process control systems, e.g., in manufacturing, environmental control, water treatment, energy management and production, consumer product goods, food and beverage production, etc. The system can allow for the rapid automatic analysis of datasets of different versions of a process.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a system comprising a plurality of computers and a plurality of storage devices storing software that when executed by the plurality of computers cause the plurality of computers to implement a plurality of subsystems comprising:

a laboratory computer subsystem comprising:
  one or more bioprocess devices configured to perform one or more respective bioprocess procedures and to generate local output data,
  a connector subsystem configured to ingest the local output data, convert the output data into a standard format;
an electronic lab notebook (ELN) subsystem that maintains an ELN database storing a plurality of ELN entries,
a bioinformatics platform subsystem that is configured to provide an ELN interface through which ELN entries are generated and modified and that maintains a data analysis subsystem for performing automatic analysis processes on one or more bioprocess datasets,
wherein the bioinformatics platform is configured to perform operations comprising:
  receiving, through the ELN interface, user input comprising a request to perform an automatic analysis process on a dataset stored by the laboratory computer subsystem,
  receiving, by the bioinformatics platform, converted data in the standard format generated by the connector subsystem executing on the laboratory computer subsystem,
  providing, by the bioinformatics platform, the converted data to the analysis subsystem,
  receiving, by the bioinformatics platform, output data from the analysis subsystem performing the analysis process,
  updating, through the ELN interface, an ELN entry that includes the output data generated by the analysis subsystem performing the analysis process on the converted data received from the connector subsystem installed on the laboratory computer system.

Embodiment 2 is the system of embodiment 1, wherein the connector subsystem is configured to ingest the local output data and convert the output data into a standard format in real-time, and wherein the bioinformatics platform is configured to perform operations in real-time.

Embodiment 3 is the system of embodiment 2, wherein the system is further configured to evaluate the output data from the analysis subsystem including performing the analysis process on the one or more bioprocess datasets to perform feedback-driven optimization of the respective bioprocess procedures of the bioprocess datasets.

Embodiment 4 is the system of any one of embodiments 1-3, wherein the data analysis subsystem is configured to receive data from external biological databases or chemical databases.

Embodiment 5 is the system of any one of embodiments 1-4, wherein the data analysis subsystem comprises pre-trained machine learning models.

Embodiment 6 is the system of any one of embodiments 1-5, wherein the data analysis subsystem is configured to generate and train machine learning models.

Embodiment 7 is the system of any one of embodiments 1-6, wherein the electronic laboratory notebook subsystem is configured to have security features configured to restrict the request to perform an automatic analysis process on a dataset stored by the laboratory computer subsystem, that can be received by a user based on the user security level.

Embodiment 8 is the system of any one of embodiments 1-7, wherein a user can create a custom automatic analysis and the system can store and use the custom automatic analysis.

Embodiment 9 is the system of any one of embodiments 1-8, wherein the analysis subsystem performing the analysis process performs the analysis process using parallel computing hardware.

Embodiment 10 is a method comprising performing the operations performed by the system of any one of claims 1-9.

Embodiment 11 is a computer storage medium encoded with a computer program, the program comprising instructions that are operable, when executed by data processing apparatus, to cause the data processing apparatus to perform the method of any one of claims 1-9.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system comprising:

a laboratory computer subsystem comprising one or more first computers and one or more first storage devices storing instructions that are operable, when executed by the one or more first computers, to cause the one or more first computers to perform first operations comprising:

performing, by one or more bioprocess devices, one or more respective bioprocess procedures to generate local output data, ingesting, by a connector subsystem installed on the laboratory computer subsystem, the local output data, converting, by the connector subsystem, the output data into a standard format of a bioinformatics platform subsystem, wherein converting the local output data to the standard format comprises transforming one or more subsets of local output data values generated by the one or more bioprocess devices of the laboratory computer subsystem into the standard format of the bioinformatics platform subsystem;

an electronic lab notebook (ELN) subsystem comprising one or more second computers and one or more second storage devices storing instructions that are operable, when executed by the one or more second computers, to cause the one or more second computers to perform second operations comprising:

maintaining an ELN database storing a plurality of ELN entries; and the bioinformatics platform subsystem comprising one or more third computers and one or more third storage devices storing instructions that are operable, when executed by the one or more third computers, to cause the one or more third computers to perform third operations comprising:

providing an ELN interface for generating or modifying ELN entries in the ELN database, receiving, through the ELN interface, user input into a worksheet corresponding to an ELN entry in the ELN database, wherein the user input represents a request to update the worksheet with results of performing an automatic analysis process on a dataset stored by the laboratory computer subsystem, in response to receiving the user input through the ELN interface, performing without further user inputs, an automatic end-to-end analysis process to update the worksheet with results of the analysis, including:

receiving, by the bioinformatics platform subsystem, converted data in the standard format generated by the connector subsystem executing on the laboratory computer subsystem, providing, by the bioinformatics platform subsystem, the converted data to an analysis subsystem installed on the bioinformatics platform subsystem, receiving, by the bioinformatics platform subsystem, output data from the analysis subsystem performing the analysis process on the converted data, and updating the ELN entry in the ELN database using the output data received from the analysis subsystem, and updating the worksheet of the ELN interface to display results of the analysis process based on the output data generated by the analysis subsystem performing the analysis process on the converted data in the standard format of the bioinformatics platform subsystem received from the connector subsystem installed on the laboratory computer system.

2. The system of claim 1, wherein converting the output data comprises ingesting the local output data and converting the output data into a standard format in real-time, and wherein the bioinformatics platform is configured to perform operations in real-time.

3. The system of claim 2, wherein the one or more third operations further comprise evaluating the output data from the analysis subsystem including performing the analysis process on one or more bioprocess datasets to perform feedback-driven optimization of the respective bioprocess procedures of the bioprocess datasets.

4. The system of claim 1, wherein the one or more third operations further comprise receiving, by the data analysis subsystem, data from external biological databases or chemical databases.

5. The system of claim 1, wherein the data analysis subsystem stores pre-trained machine learning models.

6. The system of claim 1, wherein the one or more third operations further comprise generating and training machine learning models.

7. The system of claim 1, wherein the one or more second operations comprise enforcing, by the ELN subsystem, one or more security features that restrict the request to perform an automatic analysis process on a dataset stored by the laboratory computer subsystem.

8. The system of claim 1, wherein the one or more third operations comprise performing, by the analysis subsystem, the analysis process using parallel computing hardware.

9. A method comprising:

performing, by data processing apparatus of one or more bioprocess devices of a laboratory computer subsystem comprising one or more computers, one or more respective bioprocess procedures to generate local output data;

ingesting, by a connector subsystem installed on the laboratory computer subsystem, the local output data;

converting, by the connector subsystem, the output data into a standard format of a bioinformatics platform subsystem, wherein converting the local output data to the standard format comprises transforming one or more subsets of local output data values generated by the one or more bioprocess devices of the laboratory computer subsystem into the standard format of the bioinformatics platform subsystem;

maintaining, by an electronic lab notebook (ELN) subsystem comprising one or more computers, an ELN database storing a plurality of ELN entries;

providing, by the bioinformatics platform subsystem comprising one or more computers, an ELN interface for generating or modifying ELN entries in the ELN database;

receiving, by the bioinformatics platform subsystem through the ELN interface, user input into a worksheet corresponding to an ELN entry in the ELN database, wherein the user input represents a request to update the worksheet with results of performing an automatic analysis process on a dataset stored by the laboratory computer subsystem;

in response to receiving the user input through the ELN interface, performing without further user inputs, an automatic end-to-end analysis process to update the worksheet with results of the analysis, including:

receiving, by the bioinformatics platform subsystem, converted data in the standard format generated by the connector subsystem executing on the laboratory computer subsystem;

providing, by the bioinformatics platform subsystem, the converted data to an analysis subsystem installed on the bioinformatics platform subsystem;

receiving, by the bioinformatics platform subsystem, output data from the analysis subsystem performing the analysis process on the converted data; and updating the ELN entry in the ELN database using the output data received from the analysis subsystem; and updating the worksheet of the ELN interface to display results of the analysis process based on the output data generated by the analysis subsystem performing the analysis process on the converted data in the standard format of the bioinformatics platform subsystem received from the connector subsystem installed on the laboratory computer subsystem.

10. The method of claim 9, further comprising ingesting, by the connector subsystem, the local output data and converting the output data into a standard format in real-time, and wherein the bioinformatics platform is configured to perform operations in real-time.

11. The method of claim 10, further comprising evaluating the output data from the analysis subsystem including performing the analysis process on one or more bioprocess datasets to perform feedback-driven optimization of the respective bioprocess procedures of the bioprocess datasets.

12. The method of claim 9, further comprising receiving, by the data analysis subsystem, data from external biological databases or chemical databases.

13. The method of claim 9, wherein the data analysis subsystem stores pre-trained machine learning models.

14. The method of claim 9, further comprising generating and training machine learning models by the data analysis subsystem.

15. The method of claim 9, further comprising enforcing, by the ELN subsystem, one or more security features that restrict the request to perform an automatic analysis process on a dataset stored by the laboratory computer subsystem.

16. The method of claim 9, wherein performing the analysis process by analysis subsystem comprises performing the analysis process using parallel computing hardware.

17. A plurality of non-transitory computer storage media encoded with computer program instructions that when executed by a system of a plurality of computers cause the one or more computers to perform operations comprising:

performing, by data processing apparatus of one or more bioprocess devices of a laboratory computer subsystem comprising one or more computers, one or more respective bioprocess procedures to generate local output data;

investing, by a connector subsystem installed on the laboratory computer subsystem, the local output data;

converting, by the connector subsystem, the output data into a standard format of a bioinformatics platform subsystem, wherein converting the local output data to the standard format comprises transforming one or more subsets of local output data values generated by the one or more bioprocess devices of the laboratory computer subsystem into the standard format of the bioinformatics platform subsystem;

maintaining, by an electronic lab notebook (ELN) subsystem comprising one or more computers, an ELN database storing a plurality of ELN entries;

providing, by the bioinformatics platform subsystem comprising one or more computers, an ELN interface for generating or modifying ELN entries in the ELN database;

receiving, by the bioinformatics platform subsystem through the ELN interface, user input into a worksheet corresponding to an ELN entry in the ELN database, wherein the user input represents a request to update the worksheet with results of performing an automatic analysis process on a dataset stored by the laboratory computer subsystem;

in response to receiving the user input through the ELN interface, performing without further user inputs, an automatic end-to-end analysis process to update the worksheet with results of the analysis, including:

receiving, by the bioinformatics platform subsystem, converted data in the standard format generated by the connector subsystem executing on the laboratory computer subsystem;

providing, by the bioinformatics platform subsystem, the converted data to an analysis subsystem installed on the bioinformatics platform subsystem;

receiving, by the bioinformatics platform subsystem, output data from the analysis subsystem performing the analysis process on the converted data;

updating the ELN entry in the ELN database using the output data received from the analysis subsystem; and updating the worksheet of the ELN interface to display results of the analysis process based on the output data generated by the analysis subsystem performing the analysis process on the converted data in the standard format of the bioinformatics platform subsystem received from the connector subsystem installed on the laboratory computer subsystem.

* * * * *